(12) United States Patent
Tillekeratne et al.

(10) Patent No.: US 9,862,692 B2
(45) Date of Patent: Jan. 9, 2018

(54) HIGHLY SELECTIVE ANTI-CANCER AGENTS TARGETING NON-SMALL CELL LUNG CANCER AND OTHER FORMS OF CANCER

(71) Applicant: The University of Toledo, Toledo, OH (US)

(72) Inventors: Viranga Tillekeratne, Toledo, OH (US); William Taylor, Toledo, OH (US); Sara Fedorka, North Canton, OH (US)

(73) Assignee: The University of Toledo, Toledo, OH (US)

( * ) Notice: Subject to any disclaimer, the term of this patent is extended or adjusted under 35 U.S.C. 154(b) by 0 days.

(21) Appl. No.: 14/762,259

(22) PCT Filed: Jan. 21, 2014

(86) PCT No.: PCT/US2014/012359
§ 371 (c)(1),
(2) Date: Jul. 21, 2015

(87) PCT Pub. No.: WO2014/116594
PCT Pub. Date: Jul. 31, 2014

(65) Prior Publication Data
US 2015/0344448 A1    Dec. 3, 2015

Related U.S. Application Data

(60) Provisional application No. 61/755,808, filed on Jan. 23, 2013.

(51) Int. Cl.
*C07D 277/24* (2006.01)
*C07D 277/22* (2006.01)

(52) U.S. Cl.
CPC ......... *C07D 277/24* (2013.01); *C07D 277/22* (2013.01)

(58) Field of Classification Search
CPC .......................... C07D 277/24; C07D 277/22
See application file for complete search history.

(56) References Cited

FOREIGN PATENT DOCUMENTS

WO    WO 2011012862 A1 *  2/2011

OTHER PUBLICATIONS

Geronikaki et al. Chemistry of Heterocyclic Compounds 2006, 42, 675-680.*
Lindstrom et al. Org. Lett. 2000, 2, 2291-2293.*

* cited by examiner

*Primary Examiner* — Matthew Coughlin
(74) *Attorney, Agent, or Firm* — MacMillan, Sobanski & Todd, LLC

(57) ABSTRACT

Described herein are analogs of 2-methyl-3-(2-ethynylthiazol-4-yl)cyclopent-2-enol and the corresponding ketone 3-(2-ethynylthiazol-4-yl)-2-methylcyclopent-2-enone, the analogs having terminal alkyne groups at the 2-position of the thiazole ring. These drug-like molecules, referred to as CETZOLE compounds, are useful to treat non-small cell lung cancer and other forms of cancer. Methods of making and using the compounds, methods of treating various diseases, pharmaceutical compositions, and kits are also disclosed.

2 Claims, 7 Drawing Sheets
(4 of 7 Drawing Sheet(s) Filed in Color)

HIGHLY SELECTIVE ANTI-CANCER AGENTS TARGETING NON-SMALL CELL LUNG CANCER AND OTHER FORMS OF CANCER

RELATED APPLICATIONS

The present application is a national stage application filed under 35 U.S.C. §371 of international application PCT/US14/12359, filed under the authority of the Patent Cooperation treaty on Jan. 21, 2014, published; which claims priority to U.S. Provisional Application No. 61/755,808, filed under 35 U.S.C. §111(b) on Jan. 23, 2013. The entire disclosures of all the aforementioned applications are expressly incorporated herein by reference for all purposes.

STATEMENT REGARDING FEDERALLY SPONSORED RESEARCH

The invention was not made with any government support. The government has no rights in the invention.

BACKGROUND OF THE INVENTION

Lung cancer is the leading cause of cancer death in the United States. The American Cancer Society estimates more than 240,000 new cases of lung cancer will occur, and more than 140,000 deaths will be attributed to lung cancer, in 2012. Lung cancer is categorized as either non-small cell lung carcinoma (NSCLC) or small cell lung carcinoma, with NSCLC representing more than 80% of cases.

Current treatments for lung cancer include surgery, radiation, classical chemotherapeutic agents (platinum compounds, taxanes), and targeted therapies (inhibitors of VEGFR, EGFR, IGFR, HDACS, and the proteasome). However, despite advances in treatment, five-year survival rates are about 16%. Numerous clinical trials evaluating classical chemotherapy drugs for lung cancer indicate that a therapeutic plateau with current drugs may have been reached. Therefore, there is a need for new drugs for the treatment of lung cancer that have different mechanisms of action.

SUMMARY OF THE INVENTION

Provided herein is a compound having the structural formula of Formula I or Formula II:

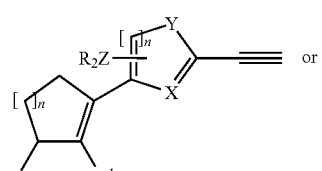

Formula I

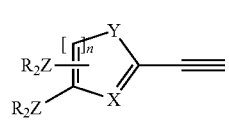

Formula II wherein n=1 or 2; X is N or CH; Y is S, O, or NH; R is =O; 2H; —$OR_3$; wherein $R_3$ is hydrogen, alkyl, aryl, glycosyl, or polyether groups; $(CO)OR_4$, wherein $R_4$ is hydrogen, alkyl, aryl, or aralkyl groups; —$NR_5R_6$, wherein $R_5$ and $R_6$ are H, alkyl, aryl, or aralkyl groups; or =N—$OR_7$, wherein $R_7$ is hydrogen, alkyl, aryl, aralkyl, glycosyl, or polyether groups; $R_1$ is hydrogen, alkyl-, aryl-, or aralkyl; Z is absent or selected from the group consisting of: halide, wherein $R_2$ is then absent; oxygen; nitrogen, wherein there are then two $R_2$ groups; (CO)O—; O(CO)—; O(CO)O—; (CO)N<, wherein there are then two $R_2$ groups; NH(CO)—; and NH(CO)N<, wherein there are then two $R_2$ groups; wherein when Z is absent, $R_2$ connects directly to a ring; and $R_2$ is hydrogen, alkyl-, aryl-, aralkyl-, glycosyl-, or polyether-, wherein multiple occurrences of $R_2$ are the same or different; and salts, stereoisomers, racemates, prodrugs, solvates, and hydrates thereof.

In certain embodiments, the compound has the structural formula of Formula III:

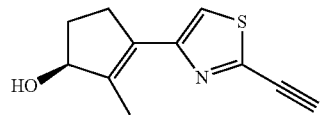

Formula III and salts, stereoisomers, racemates, prodrugs, solvates, and hydrates thereof.

In certain embodiments, the compound has the structural formula of Formula IV:

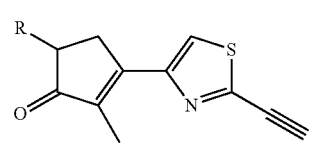

Formula IV wherein R is H, $C_6H_5CH_2$, or polyether; and salts, stereoisomers, racemates, prodrugs, solvates, and hydrates thereof.

In certain embodiments, the compound further comprises a protecting group. In particular embodiments, the protecting group is selected from the group consisting of: benzyl, t-butyl dimethyl silyl, isobutyryl, acetyl, phenoxyacetyl, allyloxycarbonyl (AOC), diisobutylformamidine, benzoyl, formyl, trifluoroacetyl, benzyloxycarbonyl (Cbz), substituted benzyloxycarbonyl, dimethoxy trityl (DMT), monomethoxytrityl (MMT), and 9-fluorenylmethyloxycarbonyl (Fmoc), t-butyloxycarbonyl (Boc), isopropyloxycarbonyl, cyclohexyloxycarbonyl, and a combination thereof. In certain embodiments, the compound comprises at least one hydroxyl protecting group. In particular embodiments, the at least one hydroxyl protecting group is selected from the group consisting of alkyl silyl groups, alkyl ethers, and esters.

Further provided is a compound having a 4-cyclopentenyl-2-ethynylthiazole skeleton and a terminal alkyne at the 2-position of the thiazole ring.

Further provided herein is a method of making a CETZOLE compound comprising subjecting a dibromothiazole to Sonogashira coupling with TMS-acetylene to obtain a silylated bromothiazole alkyne, subjecting the silylated bromothiazole alkyne to Stille coupling with an iodoalkene to obtain a silylated CETZOLE compound, and desilylating the silylated CETZOLE compound to obtain a CETZOLE compound. In certain embodiments, the dibromothiazole consists essentially of 2,4-dibromothiazole. In certain embodiments, the silylated bromothiazole alkyne consists essentially of 2-((trimethylsilyl)ethynyl)-4-bromothiazole. In certain embodiments, the iodoalkene consists essentially of 3-iodo-2-methylcyclopent-2-enone. In certain embodiments, the desilylating comprises mixing a solution of $K_2CO_3$ and the silylated CETZOLE compound in methanol for a period of time.

In certain embodiments, the method further comprises the step of subjecting the CETZOLE compound to stereoselective CBS reduction to obtain a second CETZOLE compound. In certain embodiments, the stereoselective CBS reduction comprises adding borane-$Me_2S$ to a solution of R-2-methyl-CBS-oxazaborolidine and the CETZOLE compound.

In certain embodiments, the method further comprises the steps of treating the CETZOLE compound with lithium diisopropylamide and benzyl bromide to obtain a silylated benzyl CETZOLE derivative, and desilylating the silylated benzyl CETZOLE derivative to obtain a benzylated CETZOLE compound. In certain embodiments, the silylated benzyl CETZOLE derivative consists essentially of 5-benzyl-2-methyl-3-(2-((trimethylsilyl)ethynyl)thiazol-4-yl)cyclopent-2-enone. In certain embodiments, the desilylating comprises mixing $K_2CO_3$ and MeOH with the silylated benzyl CETZOLE derivative. In certain embodiments, the benzylated CETZOLE compound consists essentially of 5-benzyl-3-(2-ethynylthiazol-4-yl)-2-methylcyclopent-2-enone.

Further provided herein is a pharmaceutical composition comprising a CETZOLE compound as described herein and a pharmaceutically acceptable carrier, diluent, or excipient.

Further provided herein is a method of treating a mammalian disease, the method comprising administering a therapeutically effective amount of a pharmaceutical composition disclosed herein to a subject in need thereof. In certain embodiments, the disease comprises cancer. In certain embodiments, the disease is non-small cell lung carcinoma (NSCLC). In certain embodiments, the disease is renal cancer. In certain embodiments, the disease is ovarian cancer. In certain embodiments, the disease is CNS cancer. In certain embodiments, the disease is melanoma.

Further provided herein is a method of treating cancer, the method comprising administering to a subject an agent that is lethal to cells by a mechanism that does not depend on apoptosis, wherein the agent comprises a compound having a 4-cyclopentyenyl-2ethynylthiazole skeleton and a terminal alkyne at the 2-position of the thiazole ring.

Further provided herein is a kit for preparing a CETZOLE compound, the kit comprising a first container housing a dibromothiazole, and a second container housing TMS-acetylene. In certain embodiments, the kit further comprises one or more of an iodoalkene, lithium diisopropylamide, or benzyl bromide.

Further provided is a composition resulting by ingestion in a compound as described herein.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the U.S. Patent and Trademark Office upon request and payment of the necessary fees.

FIG. 3A shows NCI-H522 cells exposed to compound 2 for 8 hours and stained with antibodies to tubulin. FIG. 3B shows NCI-H522 cells treated 4 times with 2 and stained with TMRE to indicate mitochondrial potential. Arrowheads: two cells that have lost mitochondrial membrane potential; phase contrast indicates these are dead cells. FIG. 3C shows quantitation of TMRE staining from microscopic images.

FIG. 5A shows cells plated in a slide-flask and analyzed by time-lapse microscopy. Interval between images shown is 1 hour. FIG. 5B shows a Kaplan-Meier plot of NCI-H522 cells exposed to compound 1f. FIG. 5C shows dose response of HOP62 and NCI-H522 exposed to compound 1f.

DETAILED DESCRIPTION OF THE INVENTION

Figure 1:
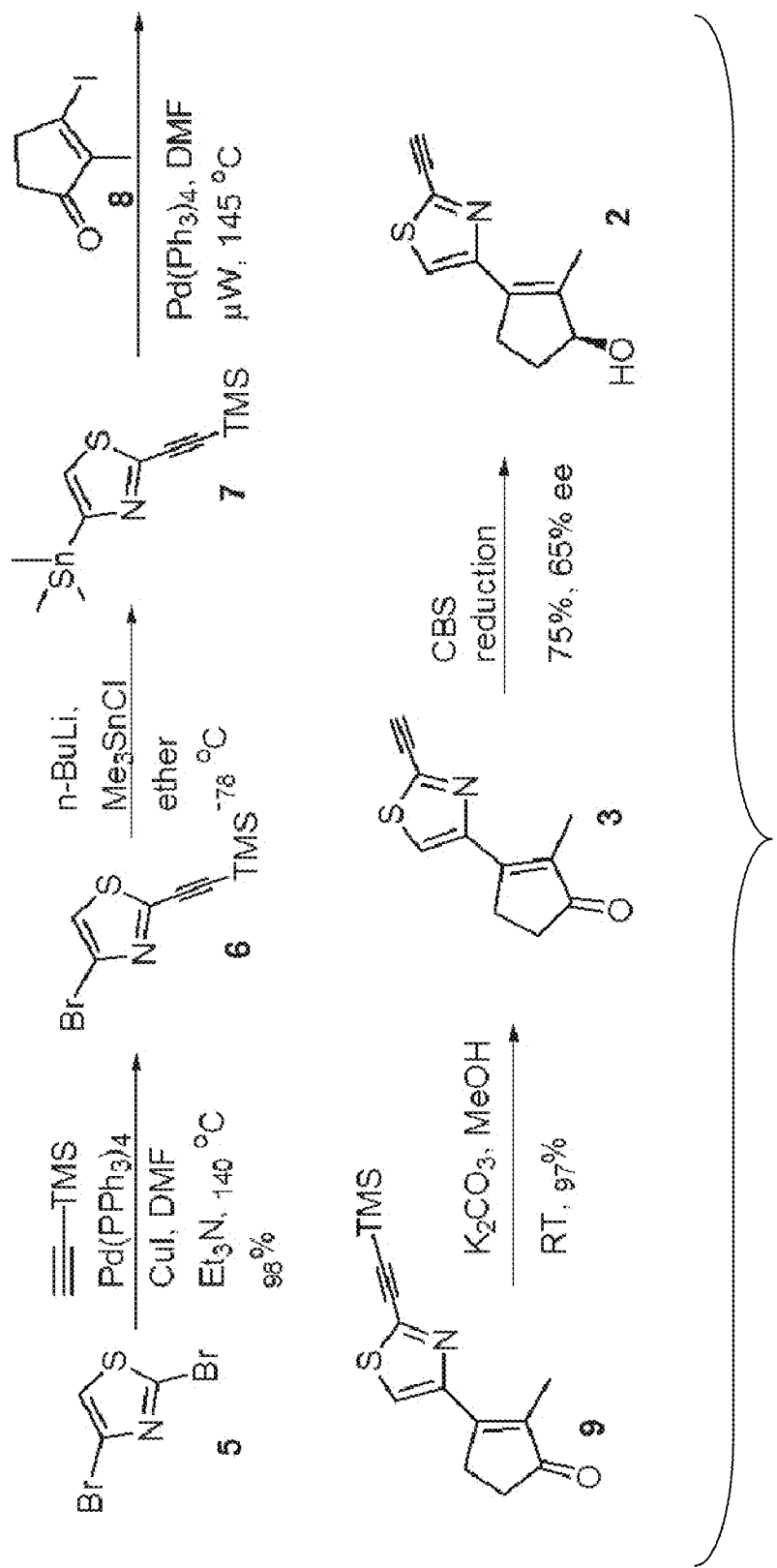
FIG. 1: Scheme of the synthetic route for compounds 2 and 3.

For convenience, various terms used herein are defined prior to further description of the various embodiments of the present disclosure.

Unless stereochemistry is specifically indicated, all stereoisomers of the compounds herein are included, as pure compounds as well as mixtures thereof.

The term "composition" as used herein is intended to encompass a product comprising the specified ingredients in the specified amounts, as well as any product that results, directly or indirectly, from combinations of the specified ingredients in the specified amounts.

The term "protecting group" as used herein refers to a group which is introduced onto a functional group in a compound and which modifies that functional group's chemical reactivity. Typically, the protecting group modifies the functional group's chemical activity in such a way that it renders the functional group chemically inert to the reaction conditions used when a subsequent chemical transformation is effected on the compound. A "hydroxyl protecting group" is accordingly a protecting group which is introduced onto a hydroxyl group in a compound.

The term "alkyl" refers to monovalent alkyl groups having from 1 to 50 carbon atoms, preferably having from 1 to 10 carbon atoms, and more preferably having from 1 to 6 carbon atoms. This term is exemplified by groups such as methyl, ethyl, n-propyl, iso-propyl, n-butyl, iso-butyl, n-hexyl, and the like. "Substituted alkyl" refers to an alkyl group, preferably of from 1 to 10 carbon atoms, having from 1 to 3 substituents selected from the group consisting of alkoxy, substituted alkoxy, acyl, acylamino, amino, aminoacyl, aminocarboxy esters, cyano, cycloalkyl, halogen, hydroxyl, carboxyl, carboxylalkyl, oxyacyl, oxyacylamino, thiol, thioalkoxy, substituted thioalkoxy, aryl, heteroaryl, heterocyclic, aryloxy, thioaryloxy, heteroaryloxy, thioheteroaryloxy, nitro, and mono- and di-alkylamino, mono- and di-(substituted alkyl)amino, mono- and di-arylamino, mono- and di-heteroarylamino, mono- and di-heterocyclic amino, and unsymmetric di-substituted amines having different substituents selected from alkyl, substituted alkyl, aryl, heteroaryl, and heterocyclic.

The term "aryl" refers to an unsaturated aromatic carbocyclic group, preferably of from 6 to 14 carbon atoms, having a single ring (e.g., phenyl) or multiple condensed rings (e.g., naphthyl or anthryl), preferably having from 1 to 3 rings. Preferred aryls include phenyl, naphthyl, and the like. Unless otherwise constrained by the definition for the aryl substituent, such aryl groups can optionally be substituted with from 1 to 3 substituents selected from the group consisting of hydroxy, acyl, alkyl, alkoxy, alkenyl, alkynyl, substituted alkyl, substituted alkoxy, substituted alkenyl, substituted alkynyl, amino, aminoacyl, aminocarboxy esters, alkaryl, aryl, aryloxy, carboxyl, carboxylalkyl, acylamino, cyano, halo, nitro, heteroaryl, heterocyclic, oxyacyl, oxyacylamino, thioalkoxy, substituted thioalkoxy, trihalomethyl, mono- and di-alkylamino, mono- and di-(substituted alkyl)amino, mono- and di-arylamino, mono- and di-heteroarylamino, mono- and di-heterocyclic amino, and unsymmetric di-substituted amines having different substituents selected from alkyl, substituted alkyl, aryl, heteroaryl, heterocyclic, and the like. Preferred substituents include alkyl, alkoxy, halo, cyano, nitro, trihalomethyl, and thioalkoxy.

The term "aralkyl" refers to alkylene-aryl groups preferably having from 1 to 10 carbon atoms in the alkylene moiety and from 6 to 10 carbon atoms in the aryl moiety. Such alkaryl groups are exemplified by benzyl, phenethyl, and the like.

The term "silyl" refers to the group $R_3Si$—, wherein each R is independently selected from H, D, C1-20 alkyl, C1-20 deuterated alkyl, fluoroalkyl, aryl, or deuterated aryl. In some embodiments, one or more carbons in an R alkyl group are replaced with Si.

The term "glycosyl" refers to free radical group obtained by removing the hemiacetal hydroxyl group from the cyclic form of a monosaccharide or lower oligosaccharide.

The term "polyether" refers to a compound that contains more than one ether group.

The term "solvate" refers to a pharmaceutically acceptable solid form of a specified compound containing solvent molecules as part of the crystal structure. A solvate typically retains at least some of the biological effectiveness of such compound. Solvates can have different solubilities, hygroscopicities, stabilities, and other properties. Examples of solvates include, but are not limited to, compounds in combination with water, isopropanol, ethanol, methanol, DMSO, ethyl acetate, acetic acid, or ethanolamine. Solvates are sometimes termed "pseudopolymorphs."

The term "hydrate" refers to a solvate with water.

The term "racemate" refers to a mixture that contains an equal amount of enantiomers.

It will be appreciated by one of ordinary skill in the art that asymmetric centers may exist in any of the compounds disclosed herein. Thus, the compounds and pharmaceutical compositions thereof may be in the form of an individual enantiomer, diastereomer, or geometric isomer, or may be in the form of a mixture of stereoisomers. In certain embodiments, the compounds are enantiopure compounds. In certain other embodiments, mixtures of stereoisomers or diastereomers are provided. Additionally, the compounds encompass both (Z) and (E) double bond isomers (or cis and trans isomers) unless otherwise specifically designated. Thus, compounds generally depicted in structures herein encompass those structures in which double bonds are (Z) or (E).

It will be appreciated that any of the compounds described herein may be substituted with any number of substituents or functional moieties. In general, the term "substituted" whether preceded by the term "optionally" or not, and substituents contained in formulas, refer to the replacement of hydrogen atoms in a given structure with a specified substituent. When more than one position in any given structure may be substituted with more than one substituent selected from a specified group, the substituent may be either the same or different at every position.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents or organic compounds. For purposes of explanation herein, heteroatoms such as nitrogen may have hydrogen substituents and/or any permissible substituents of organic compounds described herein which satisfy the valencies of the heteroatoms. Furthermore, there is not any intention to be limited in any manner by the permissible substituents or organic compounds. Combinations of substituents and variables envisioned are preferably those that result in the formation of stable compounds useful in the treatment, for example, of proliferative disorders including, but not limited to, cancer.

The term "stable" as used herein refers to compounds which possess stability sufficient to allow manufacture and which maintain the integrity of the compound for a sufficient period of time to be detected and preferably for a sufficient period of time to be useful for the purposes detailed herein.

The term "therapeutically effective amount" as used herein means that amount of active compound or pharmaceutical agent that elicits the biological or medicinal response in a tissue system, animal, or human that is being sought by a researcher, veterinarian, medical doctor, or other clinician, which includes alleviation of the symptoms of the disease or disorder being treated.

The term "pharmaceutically acceptable salt" means a salt of a compound. Suitable pharmaceutically acceptable salts of the compounds include acid addition salts which may, for example, be formed by mixing a solution of the compound with a solution of a pharmaceutically acceptable acid.

The term "pharmaceutically acceptable carrier" means a medium that is used to prepare a desired dosage form of the compound. A pharmaceutically acceptable carrier includes solvents, diluents, or other liquid vehicles; dispersion or suspension aids; surface active agents; isotonic agents; thickening or emulsifying agents; preservatives; solid binders; lubricants; and the like.

General Description

Described herein is a class of small drug-like molecules which have significant selective toxicity toward the NSCLC cell line NCI-H522 and clinical application in the treatment of many diseases such as, for example, non-small cell lung cancer, melanoma, ovarian cancer, CNS cancer, and renal cancer. Certain embodiments of these molecules rapidly kill cells in vitro, and show significant selectivity and toxicity to a subset of cell lines tested including melanoma LOX IMVI, ovarian cancer IGROV1, and renal cancer UO-31.

Described herein are compounds that are analogues of 2-methyl-3-(thiazol-4-yl)cyclopent-2-enol and 3-(2-ethynylthiazol-4-yl)-2methylcyclopent-2-enone, the compounds having terminal alkyne substituents at the 2-position of the thiazole ring. The compounds have thiazole and other aromatic ring systems with terminal alkyne groups. The thiazole substituents other than the terminal alkyne groups can be of varying hydrophobicity, hydrophilicity, and size.

In a broad aspect, the compounds of the present disclosure have the following structural formulas I or II:

Formula I

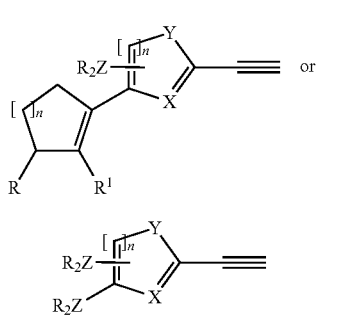

or

Formula II

and salts, stereoisomers, solvates, and hydrates thereof, where for both structures n=1 or 2; X is N or CH; Y is S, O, or NH; R is =O; 2H; —OR$_3$, wherein R$_3$ is hydrogen, alkyl, aryl, glycosyl, or polyether groups; (CO)OR$_4$, wherein R$_4$ is hydrogen, alkyl, aryl, or aralkyl groups; —NR$_5$R$_6$, wherein R$_5$ and R$_6$ are H, alkyl, aryl, or aralkyl groups; or =N—OR$_7$, wherein R$_7$ is hydrogen, alkyl, aryl, aralkyl, glycosyl, or polyether groups; R$_1$ is hydrogen, alkyl-, aryl-, or aralkyl; Z is absent or selected from the group consisting of: halide, wherein R$_2$ is then absent; oxygen; nitrogen, wherein there are then two R$_2$ groups; (CO)O—; O(CO)—; O(CO)O—; (CO)N<, wherein there are then two R$_2$ groups; NH(CO)—; and, NH(CO)N<, wherein there are then two R$_2$ groups; wherein when Z is absent, R$_2$ connects directly to the structure; and R$_2$ is hydrogen, alkyl-, aryl-, aralkyl-, glycosyl-, or polyether-, wherein multiple occurrences of R$_2$ may be the same or different.

Some of the crystalline forms for the compounds may exist as polymorphs and as such are included. In addition, some of the compounds herein may form solvates with water (i.e., hydrates) or common organic solvents, which are also included.

Protected forms of the compounds herein are further provided herein. A variety of protecting groups are possible. Suitable protecting groups include, but are not limited to: benzyl, t-butyl dimethyl silyl, isobutyryl, acetyl, phenoxyacetyl, allyloxycarbonyl (AOC), diisobutylformamidine, benzoyl, formyl, trifluoroacetyl, benzyloxycarbonyl (Cbz), substituted benzyloxycarbonyl, dimethoxy trityl (DMT), monomethoxytrityl (MMT), 9-fluorenylmethyloxycarbonyl (Fmoc), t-butyloxycarbonyl (Boc), isopropyloxycarbonyl, cyclohexyloxycarbonyl, and combinations thereof. By way of non-limiting example, a hydroxyl-protected form of the compounds are those where at least one of the hydroxyl groups is protected by a hydroxyl protecting group. Suitable hydroxyl protecting groups include, but are not limited to: alkyl silyl groups such as trimethylsilyl or tert-butyldimethylsilyl; alkyl ethers such as tetrahydropyranyl or tert-butyl; and esters such as acetate.

Prodrugs of the compounds are further provided. In general, such prodrugs are functional derivatives of the compounds that are readily convertible in vivo into the required compound. Thus, in the methods of treatment, the term "administering" includes the treatment of the various disorders described with the compound specifically disclosed or with a compound which may not be specifically disclosed, but which converts to the specified compound in vivo after administration to a subject in need thereof.

In certain embodiments, the compounds have the following structural formulas:

Formula III

Formula IV

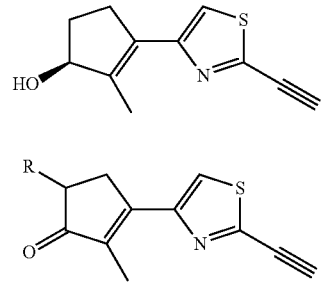

R = H, 3
R = C$_6$H$_5$CH$_2$, 4

Figure 6:
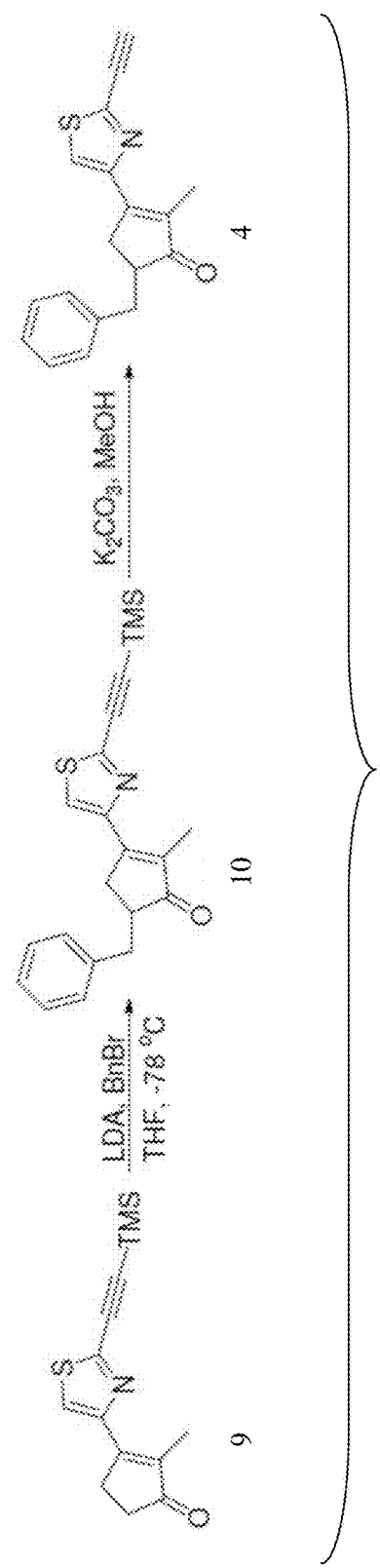
FIG. 6: Scheme showing the synthesis of 5-benzyl-3-(2-ethynylthiazol-4-yl)-2-methylcyclopent-2-enone 4.

Compound 2 (having a structural formula referred to herein as Formula III), an alcohol, shares a common 4-cyclopentenyl-2-ethynylthiazole skeleton with compound 3 (which shares a general structural formula with compound 4, the general structural formula of compounds 3 and 4 also referred to herein as Formula IV), a ketone. For ease of reference, compounds 2, 3, and 4 may therefore be referred to as CETZOLE compounds, or CETZOLEs. A non-limiting scheme of the synthesis of CETZOLEs 2 and 3 is shown in FIG. 1. As shown in FIG. 1, Sonogashira coupling of the dibromothiazole 5 with TMS-acetylene gives 6, which can be subjected to Stille coupling with the iodoalkene 8 to give 9. Desilylation of 9 with potassium carbonate in methanol gives compound 3, which can be subjected to stereoselective CBS reduction to give the alcohol 2. The stereochemistry of 2 can be confirmed using, for example, the Mosher ester model. A non-limiting scheme of the synthesis of CETZOLE 4 is shown in FIG. 6. As shown in FIG. 6, a method of synthesizing CETZOLE 4, which is the α-benzyl derivative of 3, involves treating compound 3 with lithium diisopropylamide (LDA) and benzyl bromide, then desilylating the product.

In certain embodiments, the compounds described herein show significant selectivity towards NCI-H522 cells, and are toxic only to a subset of other cell lines tested, thus making these compounds useful for the treatment of NSCLC. In certain embodiments, the compounds kill cells more rapidly and efficiently than the classical drugs adriamycin, hydroxyurea, and Taxol®. Without wishing to be bound by theory, the compounds do not overtly alter tubulin or block cells in mitosis. Rather, the compounds kill cells in a manner other than by apoptosis based on the fact that these drugs induce neither membrane blebbing nor nuclear condensation, both of which are hallmarks of apoptosis. Again without wishing to be bound by theory, it is believed the compounds have an iron-dependent mechanism of action. Thus, described herein is a method of treating mammalian diseases characterized by the undesirable proliferation of cells, the method comprising administering an agent that is lethal to the cells through mechanisms that do not depend on apoptosis, wherein the agent comprises a compound having a 4-cyclopentyenyl-2-ethynylthiazole skeleton and a terminal alkyne at the 2-position of the thiazole ring.

In certain embodiments, the toxicity of the CETZOLE compounds is elevated in cells with activation of the RAS oncogene pathway. Activating mutations in RAS are common in many types of cancer (e.g., about 15% of lung cancer and about 70% of pancreatic cancer). Accordingly, in certain embodiments, the compounds of the present disclosure exhibit outstanding clinical specificity. In certain embodiments, the toxicity of CETZOLE compounds is also elevated in cells lacking E-cadherin, which exhibit a mesenchymal phenotype. The mesenchymal/Ecadherin$^{minus}$ phenotype is associated with stem cells of various solid tumors. The selective killing of mesenchymal cells provides a way to kill cancer stem cells, thereby reducing metastatic spread and tumor relapse after therapy.

Pharmaceutical Compositions

The compounds described herein can be incorporated into pharmaceutical compositions for use in the treatment of various diseases or disorders. In certain embodiments, CETZOLE compounds 2, 3, or 4 are especially useful in pharmaceutical compositions for the treatment of non-small cell lung cancer, ovarian cancer, renal cancer, CNS cancer, or melanoma.

A pharmaceutical composition as described herein may be formulated with any of the compounds disclosed herein, plus any common excipients, diluents, or carriers. The compositions can be compressed into tablets, or formulated as elixirs or solutions for convenient oral administration or administration by intramuscular or intravenous routes. The compounds can be administered transdermally, may be formulated as sustained release dosage forms, and the like.

The compounds, compositions, and formulations provided herein are useful for treating animals, such as humans, for various diseases. A method of treating a human patient according to the present disclosure includes the administration of an effective amount of a CETZOLE compound described herein or pharmaceutical composition comprising a CETZOLE compound. The CETZOLE compounds can be formulated into compositions which may be administered by the oral and rectal routes, topically, parenterally, e.g., by injection, and by continuous or discontinuous intra-arterial infusion, in the form of, for example, tablets, lozenges, sublingual tablets, sachets, cachets, elixirs, gels, suspensions, aerosols, ointments, for example, containing from 1 to 10% by weight of the active compound in a suitable base, soft and hard gelatin capsules, suppositories, injectable solutions, and suspensions in physiologically acceptable media, and sterile packaged powders adsorbed onto a support material for making injectable solutions. Advantageously for this purpose, compositions may be provided in dosage unit form, preferably each dosage unit containing from about 5 to about 500 mg (from about 5 to about 50 mg in the case of parenteral or inhalation administration, and from about 25 to about 500 mg in the case of oral or rectal administration) the compounds. Dosages from about 0.5 to about 300 mg/kg per day, preferably 0.5 to 20 mg/kg, of active ingredient may be administered although it will, of course, readily be understood that the amount of the compound actually to be administered will be determined by a physician, in light of all the relevant circumstances including the condition to be treated, the choice of compound to be administered, and the choice of route of administration. Therefore, the dosage ranges discussed herein are not intended to limit the scope of the present invention in any way.

The formulations useful for separate administration of the CETZOLE compounds normally contain at least one CETZOLE compound (which may be referred to herein as the active ingredient or active substance) mixed with a carrier, or diluted by a carrier, or enclosed or encapsulated by an ingestible carrier in the form of a capsule, sachet, cachet, paper, or other container, or by a disposable container such as an ampoule. A carrier or diluent may be a solid, semi-solid, or liquid material which serves as a vehicle, excipient, or medium for the active therapeutic substance. Some examples of the diluents or carrier which may be employed in the pharmaceutical compositions of the present disclosure are lactose, dextrose, sucrose, sorbitol, mannitol, propylene glycol, liquid paraffin, white soft paraffin, kaolin, fumed silicon dioxide, microcrystalline cellulose, calcium silicate, silica, polyvinylpyrrolidone, cetostearyl alcohol, starch, modified starches, gum acacia, calcium phosphate, cocoa butter, ethoxylated esters, oil of theobroma, arachis oil, alginates, tragacanth, gelatin, syrup, methyl cellulose, polyoxyethylene sorbitan monolaurate, ethyl lactate, methyl and propyl hydroxybenzoate, sorbitan trioleate, sorbitan sesquioleate and oleyl alcohol, and propellants such as trichloromonofluoromethane, dichlorodifluoromethane, and dichlorotetrafluoroethane. In the case of tablets, a lubricant may be incorporated to prevent sticking and binding of the powdered ingredients in the dies and on the punch of the tableting machine. For such purpose there may be employed, for instance, aluminum, magnesium, or calcium stearates, talc, or mineral oil.

In certain embodiments, pharmaceutical compositions of the present disclosure comprise an effective amount of a CETZOLE compounds and/or additional agents, dissolved or dispersed in a pharmaceutically acceptable carrier. The phrases "pharmaceutical" or "pharmacologically acceptable" refers to molecular entities and compositions that produce no adverse, allergic, or other untoward reaction when administered to an animal, such as, for example, a human. The preparation of a pharmaceutical composition that contains at least one compound or additional active ingredient will be known to those of skill in the art in light of the present disclosure, as exemplified by Remington's Pharmaceutical Sciences, 2003, incorporated herein by reference. Moreover, for animal (e.g., human) administration, it will be understood that preparations should meet sterility, pyrogenicity, and general safety and purity standards as required by FDA Office of Biological Standards.

A composition disclosed herein may comprise different types of carriers depending on whether it is to be administered in solid, liquid, or aerosol form, and whether it needs to be sterile for such routes of administration as injection. Compositions disclosed herein can be administered intravenously, intradermally, transdermally, intrathecally, intraarterially, intraperitoneally, intranasally, intravaginally, intrarectally, intraosseously, periprosthetically, topically, intramuscularly, subcutaneously, mucosally, in utero, orally, topically, locally, via inhalation (e.g., aerosol inhalation), by injection, by infusion, by continuous infusion, by localized perfusion bathing target cells directly, via a catheter, via a lavage, in cremes, in lipid compositions (e.g., liposomes), or by other method or any combination of the forgoing as would be known to one of ordinary skill in the art.

The actual dosage amount of a composition disclosed herein administered to an animal or human patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The compounds of the present disclosure are generally effective over a wide dosage range. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein. Naturally, the amount of active compound(s) in each therapeutically useful composition may be prepared in such a way that a suitable dosage will be obtained in any given unit dose of the compound. Factors such as solubility, bioavailability, biological half-life, route of administration, product shelf life, as well as other pharmacological considerations, will be contemplated by those preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain embodiments, a composition and/or additional agent is formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsules, or they may be compressed into tablets, or they may be incorporated directly with the food of the diet.

In further embodiments, a composition described herein may be administered via a parenteral route. As used herein, the term "parenteral" includes routes that bypass the alimentary tract. Specifically, the pharmaceutical compositions disclosed herein may be administered, for example but not limited to, intravenously, intradermally, intramuscularly, intraarterially, intrathecally, subcutaneous, or intraperitoneally (U.S. Pat. Nos. 6,753,514; 6,613,308; 5,466,468; 5,543,158; 5,641,515; and 5,399,363 are each specifically incorporated herein by reference in their entirety).

Solutions of the compositions disclosed herein as free bases or pharmacologically acceptable salts may be prepared in water suitably mixed with a surfactant, such as hydroxypropylcellulose. Dispersions may also be prepared in glycerol, liquid polyethylene glycols, and mixtures thereof, and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form should be sterile and should be fluid to the extent that easy injectability exists. It should be stable under the conditions of manufacture and storage and should be preserved against the contaminating action of microorganisms, such as bacteria and fungi. The carrier can be a solvent or dispersion medium containing, for example, water, ethanol, a polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it is preferable to include isotonic agents, such as, but not limited to, sugars or sodium chloride. Prolonged absorption of the injectable compositions can be brought about by the use in the compositions of agents delaying absorption such as, for example, aluminum monostearate, or gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. Sterile aqueous media that can be employed will be known to those of skill in the art in light of the present disclosure. For example, one dosage may be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

Sterile injectable solutions are prepared by incorporating the compositions in the required amount in the appropriate solvent with various other ingredients enumerated above, as required, followed by filtered sterilization. Generally, dispersions are prepared by incorporating the various sterilized compositions into a sterile vehicle which contains the basic dispersion medium and the required other ingredients from those enumerated above. In the case of sterile powders for the preparation of sterile injectable solutions, some methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

In other embodiments, the compositions may be formulated for administration via various miscellaneous routes, for example, topical (i.e., transdermal) administration, mucosal administration (intranasal, vaginal, etc.) and/or via inhalation. Pharmaceutical compositions for topical administration may include the compositions formulated for a medicated application such as an ointment, paste, cream or powder. Ointments include all oleaginous, adsorption, emulsion, and water-soluble based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones, and luarocapram. Possible bases for compositions for topical application include polyethylene glycol, lanolin, cold cream, and petrolatum as well as any other suitable absorption, emulsion, or water-soluble ointment base. Topical preparations may also include emulsifiers, gelling agents, and antimicrobial preservatives as necessary to preserve the composition and provide for a homogenous mixture. Transdermal administration of the compositions may also comprise the use of a "patch." For example, the patch may supply one or more compositions at a predetermined rate and in a continuous manner over a fixed period of time.

In certain embodiments, the composition is in a form which is suitable for application to human skin. In certain embodiments, the composition is in the form of an oil, ointment, cream, lotion, or gel. In certain embodiments, the composition contains, as additional ingredients, any of: water, oil, alcohols (such as ethanol, isopropanol, or propanol), emulsifying agents, perfumes, coloring agents, fillers, abrasive agents, moisturizers, or combinations thereof.

In certain embodiments, the compositions are suitable for delivery by eye drops, intranasal sprays, inhalation, and/or other aerosol delivery vehicles. Methods for delivering compositions directly to the lungs via nasal aerosol sprays have been described in U.S. Pat. Nos. 5,756,353 and 5,804,212 (each specifically incorporated herein by reference in their entirety). Likewise, the delivery of drugs using intranasal microparticle resins (Takenaga et al., 1998) and lysophosphatidyl-glycerol compounds (U.S. Pat. No. 5,725,871 specifically incorporated herein by reference in its entirety) are also well-known in the pharmaceutical arts and could be employed to deliver the compositions described herein. Likewise, transmucosal drug delivery in the form of a polytetrafluoroetheylene support matrix is described in U.S. Pat. No. 5,780,045 (specifically incorporated herein by reference in its entirety), and could be employed to deliver the compositions described herein.

It is further envisioned the compositions disclosed herein may be delivered via an aerosol. The term aerosol refers to a colloidal system of finely divided solid or liquid particles dispersed in a liquefied or pressurized gas propellant. The typical aerosol for inhalation consists of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight, and the severity and response of the symptoms.

In a composition, the CETZOLE compound may be in free form or, where appropriate, as pharmaceutically acceptable derivatives such as prodrugs, salts, and/or esters of the compound. The composition may be in any suitable form such as solid, semisolid, or liquid form. In general, the pharmaceutical preparation will contain one or more of the compounds as an active ingredient in an admixture with an organic or inorganic carrier or excipient suitable for external, enteral, or parenteral application. The active ingredient may be compounded, for example, with the usual non-toxic, pharmaceutically acceptable carriers for tablets, pellets, capsules, suppositories, pessaries, solutions, emulsions, suspensions, and any other form suitable for use. The carriers that can be used include water, glucose, lactose, gum acacia, gelatin, mannitol, starch paste, magnesium trisilicate, talc, cornstarch, keratin, colloidal silica, potato starch, urea, and other carriers suitable for use in manufacturing preparations, in solid, semi-solid, or liquefied form. In addition, auxiliary stabilizing, thickening, and coloring agents may be used.

Pharmaceutical preparations can include at least one of the compounds as described herein, or a pharmaceutically acceptable derivative thereof, which compounds are capable of inhibiting the growth of or killing cancer cells, and, in certain embodiments, are capable of inhibiting the growth of or killing multidrug-resistant cancer cells. In certain embodiments, the pharmaceutical preparations also comprise a solubilizing or emulsifying agent.

In one aspect, the compounds and compositions are used to treat cancers such as non-small cell lung cancer, renal cancer, ovarian cancer, CNS cancer, and melanoma. The method of treatment comprises administering a therapeutically effective amount of a compound to a subject suffering from cancer or other disease. The method may be repeated as necessary either to mitigate (i.e., prevent further growth) or to eliminate the cancer. Clinically, practice of the method will result in a reduction in the size or number of the cancerous growth and/or a reduction in associated symptoms (where applicable). Pathologically, practice of the method will produce at least one of the following: inhibition of cancer cell proliferation, reduction in the size of the cancer or tumor, prevention of further metastasis, and inhibition of tumor angiogensis.

The compounds and compositions can be used in combination therapies. That is, the compounds and compositions can be administered concurrently with, prior to, or subsequent to one or more other desired therapeutic or medical procedures or drugs. The particular combination of therapies and procedures in the combination regimen will take into account compatibility of the therapies and/or procedures and the desired therapeutic effect to be achieved. Combination therapies include sequential, simultaneous, and separate administration of the active compound in a way that the therapeutic effects of the first administered procedure or drug is not entirely disappeared when the subsequent procedure or drug is administered.

By way of a non-limiting example of a combination therapy, the CETZOLE compounds or compositions can be administered in combination with one or more suitable anti-cancer agents including, but not limited to: chemotherapeutic agents; cytotoxins; antimetabolites; alkylating agents; protein kinase inhibitors; anthracyclines; antibiotics; antimitotic agents (e.g. antitubulin agents); corticosteroids; radiopharmaceuticals; proteins such as cytokines, enzymes, or interferons; biological response modifiers such as krestin, lentinan, sizofiran, picibanil, ubenimex; anti-angiogenic compounds such as acitretin, fenretinide, thalidomide, zoledronic acid, angiostatin, aplidine, cilengtide, combretastatin A-4, endostatin, halofuginone, rebimastat, Removab®, Revlimid®, squalamine, ukrain, or Vitaxin®; platinum-coordinated compounds such as cisplatin, carboplatin, nedaplatin, or oxaliplatin; camptothecin derivatives such as camptothecin, 10-hydroxycamptothecin, 9-aminocamptothecin, irinotecan, SN-38, edotecarin, or topotecan; compounds or chelates that include radionuclides; or combinations thereof. Examples of suitable interferons include, but are not limited to interferon alpha, interferon alpha-2a, interferon, alpha-2b, interferon beta, interferon gamma-1a, interferon gamma-1b (Actimmune), interferon gamma-n1, or combinations thereof.

In certain embodiments, the anti-cancer agent is one or more of hydroxyureas, Taxol®, adriamycin, 5-fluorouracil, cyclophosphamide, etoposide, altretamine, ifosfamide, vinblastine sulfate, estramustine phosphate, suramin, strontium-89, filgrastim, lentinan, sizofilan, TheraCys®, ubenimex, WF-10, aldesleukin, alemtuzumab, BAM-002, dacarbazine, daclizumab, denileukin, gemtuzumab ozogamicin, ibritumomab, imiquimod, lenograstim, lentinan, Corixa, molgramostim, OncoVAX-CL, sargramostim, tasonermin, tecleukin, thymalasin, tositumomab, Virulizin®, Z-100, epratuzumab, mitumomab, oregovomab, pemtumomab (Y-muHMFG1), Provenge® (Dendreon), alitretinoin, ampligen, atrasentan bexarotene, bortezomib, bosentan, calcitriol, exisulind, finasteride, fotemustine, ibandronic acid, miltefosine, mitoxantrone, 1-asparaginase, procarbazine, dacarbazine, hydroxycarbamide, pegaspargase, pentostatin, tazarotne, Telcyta® (TLK-286, Telik Inc.), Velcade® (bortemazib, Millenium), or tretinoinor.

Another non-limiting example of a combination therapy for NSCLC or other cancers is the combination of a CETZOLE compound or CETZOLE-containing composition with one or more surgical treatments. Suitable surgical treatments include, but are not limited to, a wedge resection, a lobectomy, a pneumonectomy, a sleeve reduction, a hysterectomy, a bilateral salpingo-oophorectomy, an omentectomy, or a nephrectomy. Other possible therapies suitable for combination with a CETZOLE compound or CETZOLE-containing composition include, but are not limited to, immunotherapy, hormone therapy, radiation therapy, or a combination thereof.

Embodiments of the present disclosure further include methods of determining coverage or denial of health insurance reimbursement and/or payment for treatments of disease comprising the compounds or compositions described herein. In certain embodiments, the treatment comprises a CETZOLE compound or CETZOLE-containing pharmaceutical composition, and a provider of health insurance denies coverage or reimbursement for the treatment.

Kits

The compounds or methods described herein could be embodied as parts of a kit or kits. A non-limiting example of such a kit comprises one or more CETZOLE compounds and a pharmaceutically acceptable carrier, diluent, or excipient in separate containers, where the containers may or may not be present in a combined configuration. Many other kits are possible, such as kits for preparing a CETZOLE compound. In certain embodiments, a kit for preparing a CETZOLE compound comprises a dibromothiazole and TMS-acetylene in separate containers. In particular embodiments, the kit further comprises an iodoalkene, lithium diisopropylamide, benzyl bromide, or combinations thereof.

The kits may further include instructions for using the components of the kit(s) to practice the subject methods. The instructions for practicing the subject methods are generally recorded on a suitable recording medium. For example, the instructions may be present in the kits as a package insert or in the labeling of the container of the kit or components thereof. In other embodiments, the instructions are present as an electronic storage data file present on a suitable computer readable storage medium, such as a flash drive, CD-ROM, or diskette. In other embodiments, the actual instructions are not present in the kit, but means for obtaining the instructions from a remote source, such as via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

Synthesis of Compounds 2 and 3

A mixture of commercially available 2,4-dibromothiazole 5 (3.000 g, 12.34 mmol, 1 equiv), triphenylphosphine (486 mg, 1.851 mmol, 5 mol %), CuI (120 mg, 0.617 mmol, 5 mol %), and Pd(PPh$_3$)$_2$Cl$_2$ (120 mg, 0.173 mmol, 1.4 mol %) was placed in a three-neck roundbottom flask under nitrogen. Anhydrous toluene (42 mL) was added followed by anhydrous Et$_3$N (2.2 mL, 15.04 mmol, 1.3 equiv) and trimethylsilylacetylene (2.6 mL, 18.51 mmol, 1.5 equiv). The reaction mixture was refluxed at 140° C. for 2 d. It was poured into water (50 mL) and extracted with EtOAc (3×20 mL). The combined organic extract was dried over anhydrous sodium sulfate and concentrated in vacuo. The crude product was purified by flash chromatography on silica gel in CH$_2$Cl$_2$-hexanes to obtain 6 (2.625 g, 81%) as a brownish/red solid: TLC R$_f$=0.72 (10% EtOAc-hexanes); mp 37° C.; IR: 3300, 2900, 2250 cm$^{-1}$; $^1$H NMR (400 MHz, CDCl$_3$): δ 7.18 (s, 1H), 0.24 (s, 9H); $^{13}$C NMR (CDCl$_3$, 100 MHz): δ 149.54, 125.87, 118.85, 103.03, 95.52, −0.41; HRMS (m/z): [M+H]$^+$ calculated for C$_8$H$_{11}$NSSiBr, 259.9565; found, 259.9565.

A solution of 2-((trimethylsilyl)ethynyl)-4-bromothiazole 6 (100 mg, 0.384 mmol, 1 equiv) in anhydrous ether (3 mL) under N$_2$ was cooled to −78° C. and t-BuLi (240 μL, 1.6 M, 0.786 mmol, 1 equiv) was added dropwise. The reaction mixture was stirred at −78° C. for 1 hr and a solution of trimethyltin chloride (150 mg, 0.768 mmol, 2 equiv) in anhydrous ether (2 mL) was added via syringe. The reaction mixture was stirred at −78° C. for an additional 1 hour and was allowed to warm to room temperature slowly. The reaction mixture was diluted with hexanes, passed through a silica gel pad deactivated with 5% Et$_3$N-hexanes, eluted with EtOAc, and concentrated in vacuo to obtain a yellow oil 7, which was immediately taken to the next step. $^1$H NMR (600 MHz, CDCl$_3$): δ 7.33 (s, 1H), 0.34 (t, J=14.8 Hz, 9H), 0.25 (m, 3H).

3-Iodo-2-methylcyclopent-2-enone 8 (83 mg, 3.84 mmol, 1 equiv) and Pd(PPh$_3$)$_4$ (88 mg, 0.078 mmol, 20 mol %) were placed in a μw vial under N$_2$. A solution of tin derivative 7 prepared above in dry DMF (2 mL) was added via syringe. The μw vial was heated for 2 hours and 15 minutes in a microwave synthesizer at 145° C. The reaction mixture was poured into water (30 mL) and extracted with EtOAc (3×, 10 mL). The combined organic extract was dried over anhydrous sodium sulfate and concentrated in vacuo. The crude product was purified by flash chromatography on silica gel in EtOAc-hexanes and recrystallized from CH$_2$Cl$_2$-hexanes to obtain 9 as tan, star-shaped crystals (50 mg, 47%): TLC R$_f$=0.63 (40% EtOAc-hexanes); mp 108-110° C.; IR: 3300, 2900, 2200, 1750 cm$^{-1}$; $^1$H NMR (600 MHz, CDCl$_3$): δ 7.58 (s, 1H), 2.99 (t, J=2.0 Hz, 2H), 2.52 (m, 2H), 2.10 (d, J=2.0 Hz, 3H), 0.28 (s, 9H); $^{13}$C NMR (CDCl$_3$, 100 MHz): δ 209.71, 157.66, 152.65, 148.22, 137.37, 121.79, 102.05, 96.15, 33.74, 28.18, 10.23, −0.46; HRMS (m/z): [M+Na]$^+$ calculated for C$_{14}$H$_{17}$NOSSi, 298.0698; found, 298.0680.

A solution of 2-methyl-3-(2-((trimethylsilyl)ethynyl)thiazol-4-yl)cyclopent-2-enone 9 (50 mg, 0.182 mmol, 1 equiv) and K$_2$CO$_3$ (3 mg, 0.022 mmol, 12 mol %) in methanol (1 mL) was stirred for 5 minutes. The crude product was poured into water (8 mL) and extracted with EtOAc (3×, 3 mL). The combined organic extract was dried over anhydrous sodium sulfate and concentrated in vacuo. The product was recrystallized from CH$_2$Cl$_2$-hexanes to obtain 3 as tan needles: TLC R$_f$=0.33 (40% EtOAc-hexanes); mp 138-139° C.; IR: V$_{max}$ 3000, 2900, 2250, 1750 cm$^{-1}$; $^1$H NMR (400 MHz, CDCl$_3$): δ 7.62 (s, 1H), 3.52 (s, 3H), 2.99-2.96 (m, 2H), 2.53-2.51 (m, 2H), 2.11 (t, J=2.0 Hz, 3H); $^{13}$C NMR (CDCl$_3$, 100 MHz): δ 209.98, 157.56, 153.08, 147.50, 137.84, 121.90, 83.24, 76.31, 33.92, 28.31, 10.38; HRMS (m/z): [M+Na]$^+$ calculated for C$_{11}$H$_9$NOS, 226.0303; found, 226.0298.

A solution of 3-(2-ethynylthiazol-4-yl)-2-methylcyclopent-2-enone 3 (95 mg, 0.340, 1 equiv) and R-2-methyl-CBS-oxazaborolidine (19 mg, 0.072 mmol, 20 mol %) in anhydrous THF (2 mL) was cooled to 0° C. A solution of borane-Me$_2$S (170 μL, 0.340 mmol, 1 equiv) in THF was added dropwise. The reaction mixture was stirred at 0° C. for 25 minutes and the reaction was quenched by slow addition of water (5 mL) at 0° C. The reaction mixture was extracted with EtOAc (3×2 mL). The combined organic extract was dried over anhydrous sodium sulfate and concentrated in vacuo. The crude product was purified by preparative thin-layer chromatography on silica gel in 25% EtOAc-CH$_2$Cl$_2$ to obtain the partial purified product 2 (72 mg, 75.1%) as a reddish/brown solid: TLC R$_f$=0.58 (40% EtOAc-CH$_2$Cl$_2$); mp 69-71° C.; [α]$^{25}_D$=-12.8° (c=1.50, CHCl$_3$); IR: V$_{max}$ 3300, 2900, 2300 cm$^{-1}$; $^1$H NMR (400 MHz, CDCl$_3$): δ 7.13 (s, 1H), 4.73 (d, J=4.4 Hz, 1H), 3.44 (s, 1H), 2.88-2.81 (m, 1H), 2.67-2.60 (m, 1H), 2.43-2.34 (m, 1H), 2.14 (d, J=8.8 Hz, 3H), 1.78-1.70 (m, 1H); $^{13}$C NMR (CDCl$_3$, 100 MHz): δ 154.15, 146.52, 140.24, 130.83, 117.48, 82.30, 82.14, 32.91, 32.67, 13.49; HRMS (m/z): [M+Na]$^+$ calculated for C$_{11}$H$_{11}$NOS, 228.0458; found, 228.0459.

Synthesis of Compound 4 n-BuLi (333 μL, 0.841 mmol, 1.2 equiv) was added to a solution of anhydrous diisopropyl amine (120 μL, 0.841 mmol, 1.2 equiv) in anhydrous THF (3 mL) at −78° C. The reaction mixture was stirred at −78° C. for 5 min and then stirred at 0° C. for 30 minutes. A solution of 2-methyl-3-(2-((trimethylsilyl)ethynyl)thiazol-4-yl)cyclopent-2-enone 9 (193 mg, 0.700 mmol, 1 equiv) in anhydrous THF (3 mL) was added. The reaction mixture was stirred for 10 min at 0° C., warmed to room temperature, was stirred for 10 min, and benzyl bromide (180 μL, 1.54 mmol, 2.2 equiv) was added. The reaction mixture was stirred at room temperature overnight. It was then poured into water (10 mL) and extracted with ethyl acetate (3×5 mL). The combined organic extract was dried over anhydrous sodium sulfate, and the solvent was removed in vacuo. The product was purified by flash chromatography on silica gel in EtOAc-hexanes followed by preparative thin-layer chromatography on silica gel in 20% EtOAc-hexanes to obtain the dibenzylated product and the monobenzylated product 10: (3.9 mg), mp 153-155° C.; $^1$H NMR (400 MHz, CDCl$_3$): δ 7.56 (s, 1H), 7.30-7.26 (m, 2H), 7.23-7.19 (m, 3H), 3.36 (dd, J=14.0 Hz, 4.0 Hz, 1H), 3.03-3.01 (m, 1H), 2.86-2.83 (m, 1H), 2.73-2.68 (m, 1H), 2.60-2.54 (m, 1H), 2.14 (t, J=2.0 Hz, 3H), 0.28 (t, J=3.6 Hz, 9H); $^{13}$C NMR (CDCl$_3$, 100 MHz) δ 210.94, 156.79, 148.40, 139.82, 136.68, 129.07, 128.68, 126.51, 122.06, 102.33, 96.18, 46.33, 37.58, 434.85, 10.56, −0.31.

A mixture of 5-benzyl-2-methyl-3-(2-((trimethylsilyl)ethynyl)thiazol-4-yl)cyclopent-2-enone 10 (3.9 mg, 0.11 mmol, 1.0 equiv), K$_2$CO$_3$ (0.26 mg, 0.002 mmol, 18 mol %) and MeOH (100 μL) was stirred at room temperature for 10 min. Water (500 μL) was added and the mixture was extracted with EtOAc (3×500 μL). The combined organic extract was concentrated in vacuo and the product was purified by preparative thin-layer chromatography on silica gel in 20% EtOAc-hexanes to obtain 4 as a yellow solid (2.3 mg); $^1$H NMR (400 MHz, CDCl$_3$): δ 7.54 (s, 1H), 7.29-7.25 (m, 2H), 7.22-7.17 (m, 3H), 3.50 (s, 1H), 3.33 (dd, J=14.0 Hz, 4.4 Hz, 1H), 3.05-2.99 (m, 1H), 2.86-2.80 (m, 1H), 2.71-2.65 (m, 1H), 2.59 (dd, J=10.4 Hz, 3.2 Hz, 1H), 2.13 (t, J=2.0 Hz, 3H); $^{13}$C NMR (CDCl$_3$, 100 MHz) δ 210.86, 156.36, 152.98, 147.47, 139.78, 136.94, 130.12, 128.62, 126.53, 122.12, 83.22, 76.27, 46.30, 37.56, 34.72, 10.51.

Biological Activity and Selectivity

The compounds described herein were evaluated in comparison to the following open-chain epothilones:

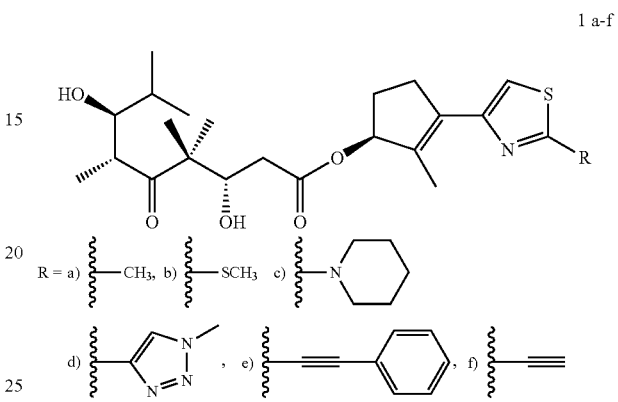

1 a-f

Figure 4:
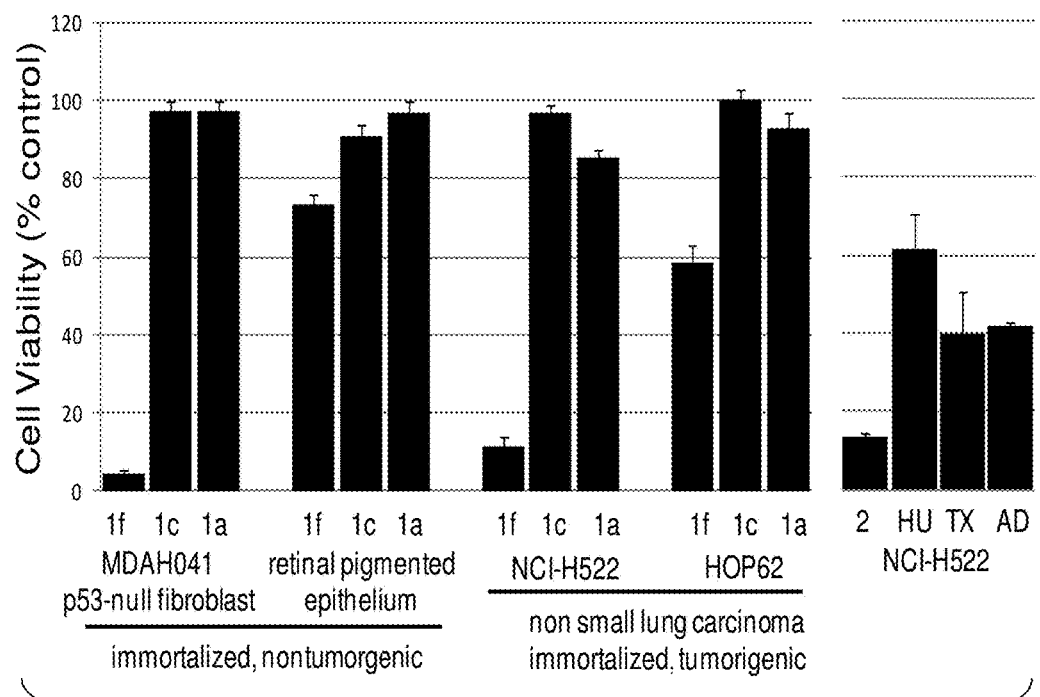
FIG. 4: The effects of compounds 1f, 1c, and 1a on cell viability, in comparison with the effects on cell viability of compound 2 and the drugs hydroxyurea, Taxol®, and adriamycin.
Figure 5A:
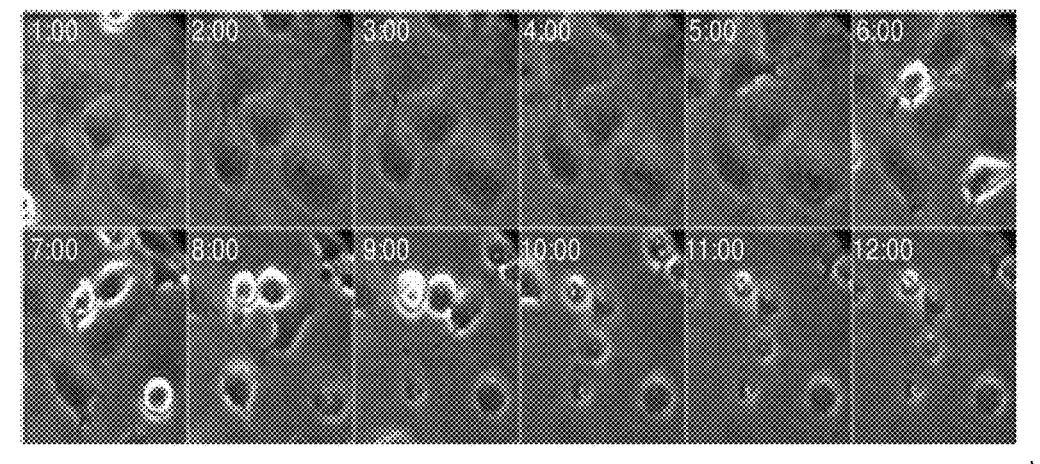
FIGS. 5A-5C: The effect of compound 1f on NCI-H522 cells at 10 μM.
Figure 5B:
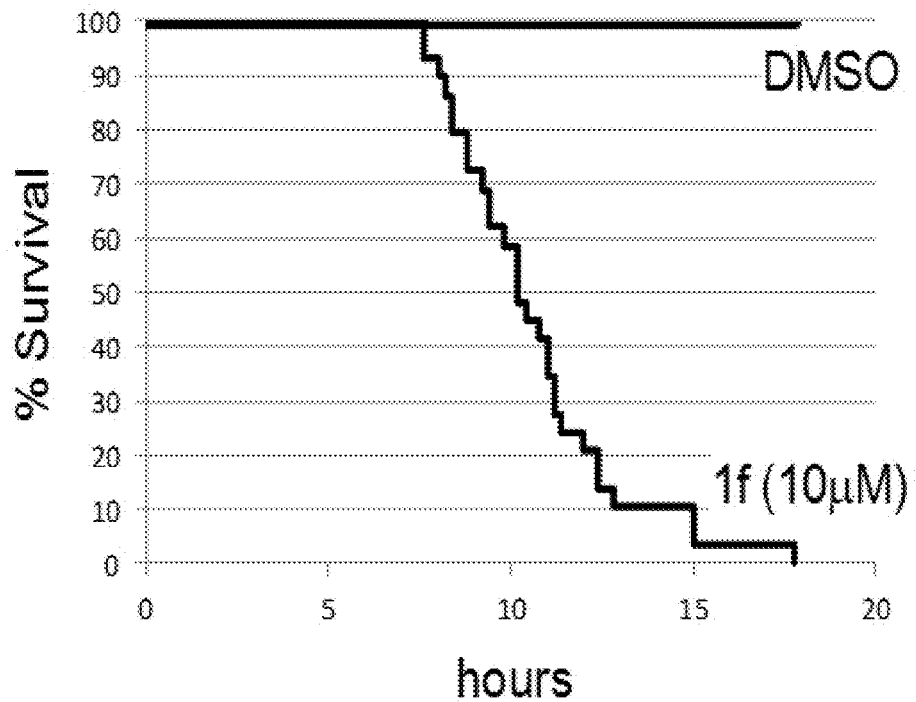
Figure 5C:
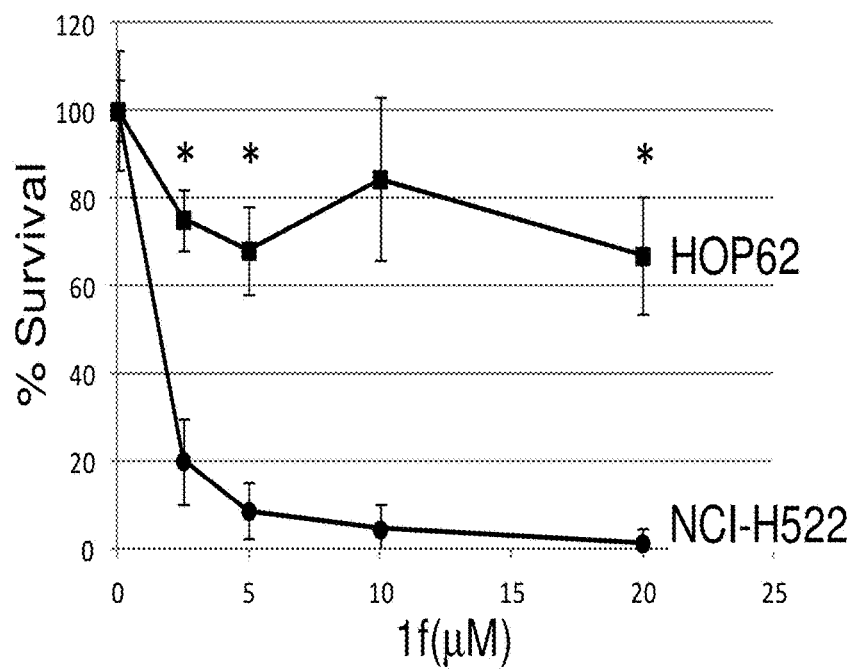

From these compounds, 1f was lethal against non-small cell lung cancer cell lines HOP62 (75%) and NCI-H522 (62%), CNS cancer U251 (25%), melanoma LOX IMVI (23%), ovarian cancer IGROV1 (32%), and renal cancer UO-31 (36%). NCI-H522 cells treated with 1f at 10 μM were killed completely after 18 hours of treatment. Compound 1f killed NCI-H522 cells with an LD$_{50}$ of 1 μM—more than 20 times lower than the estimated LD$_{50}$ for HOP62 cells. However, compounds 1a, 1b, 1c, and 1d had little effect at 10 μM even after several days of treatment. The cytotoxic effect of 1f is due to the alcohol 2 formed by in situ hydrolysis of the ester 1f. FIG. 4 displays the effects of compounds 1a, 1c, 1f and 2 on cell viability, in comparison with the drugs hydroxyureas, Taxol®, and adriamycin. FIGS. 5A-5C show the effects of 1f on NCI-H522 cells at 10 μM.

Figure 3A:
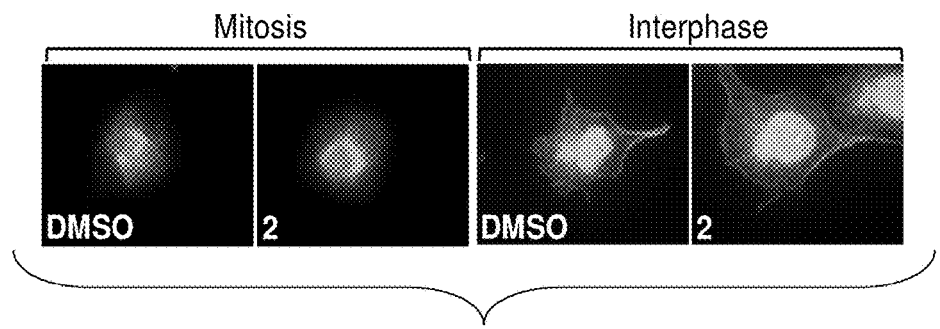
FIGS. 3A-3C: The effect of compound 2 (10 μM) on tubulin and mitochondrial function.
Figure 3B:
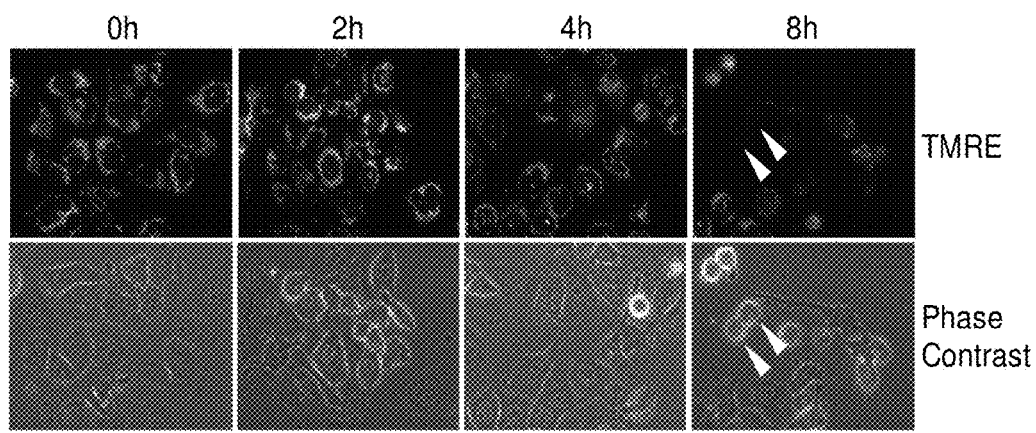
Figure 3C:
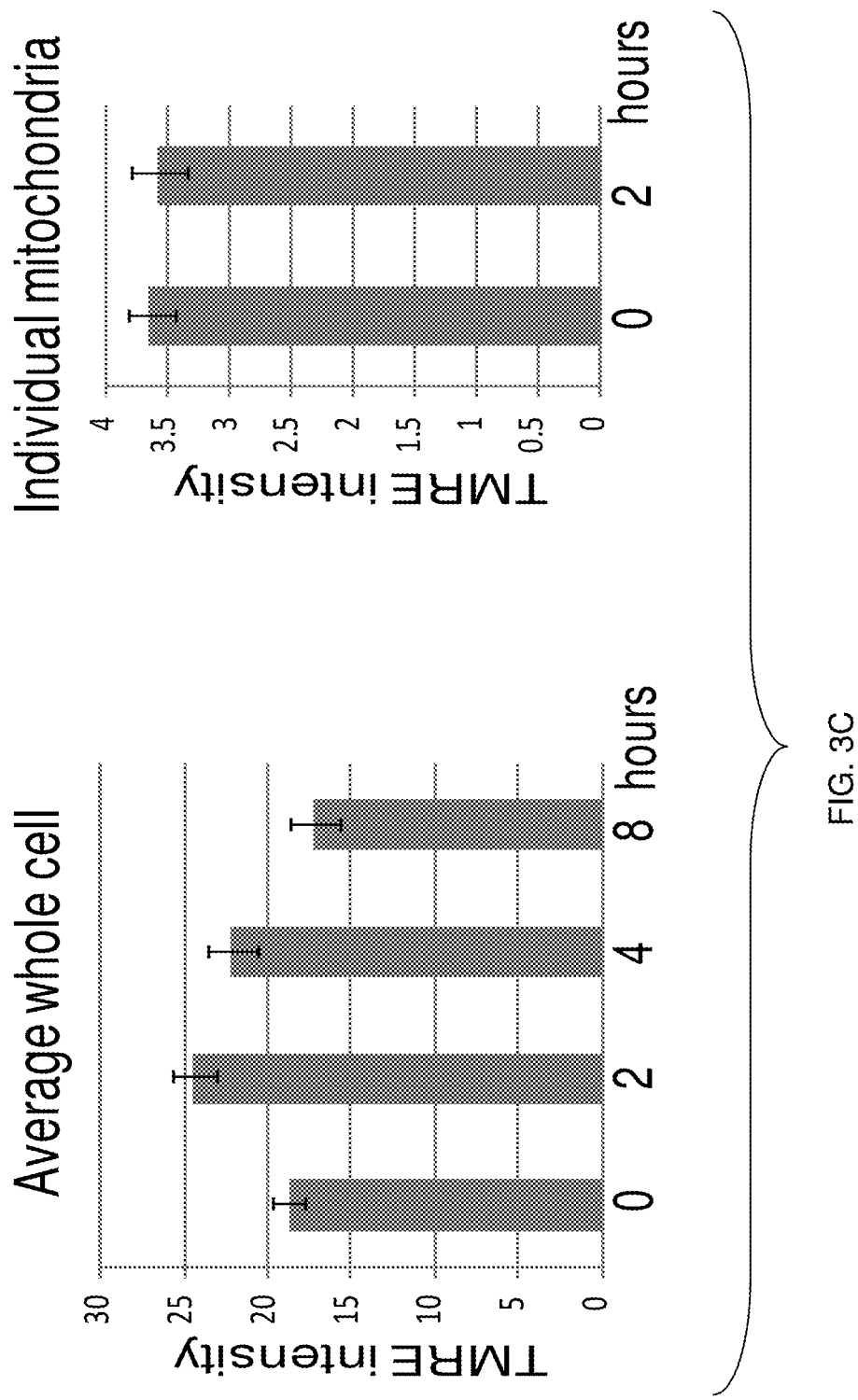

The effects of compound 2 on NCI-H522 cells, other cancer cells, and normal cell lines were evaluated. Compound 2 killed NCI-H522 cells at 10 μM. Cell staining showed compound 2 had no overt effects on tubulin in interphase or mitosis, thus showing that compound 2 does not mimic epothilones in mechanism of action. FIGS. 3A-3C show the effects of compound 2 on tubulin and mitochondrial function. The rapid mode of cell death shows compound 2 could disrupt mitochondrial function. However, membrane potentials were intact until late in the death process.

Figure 2:
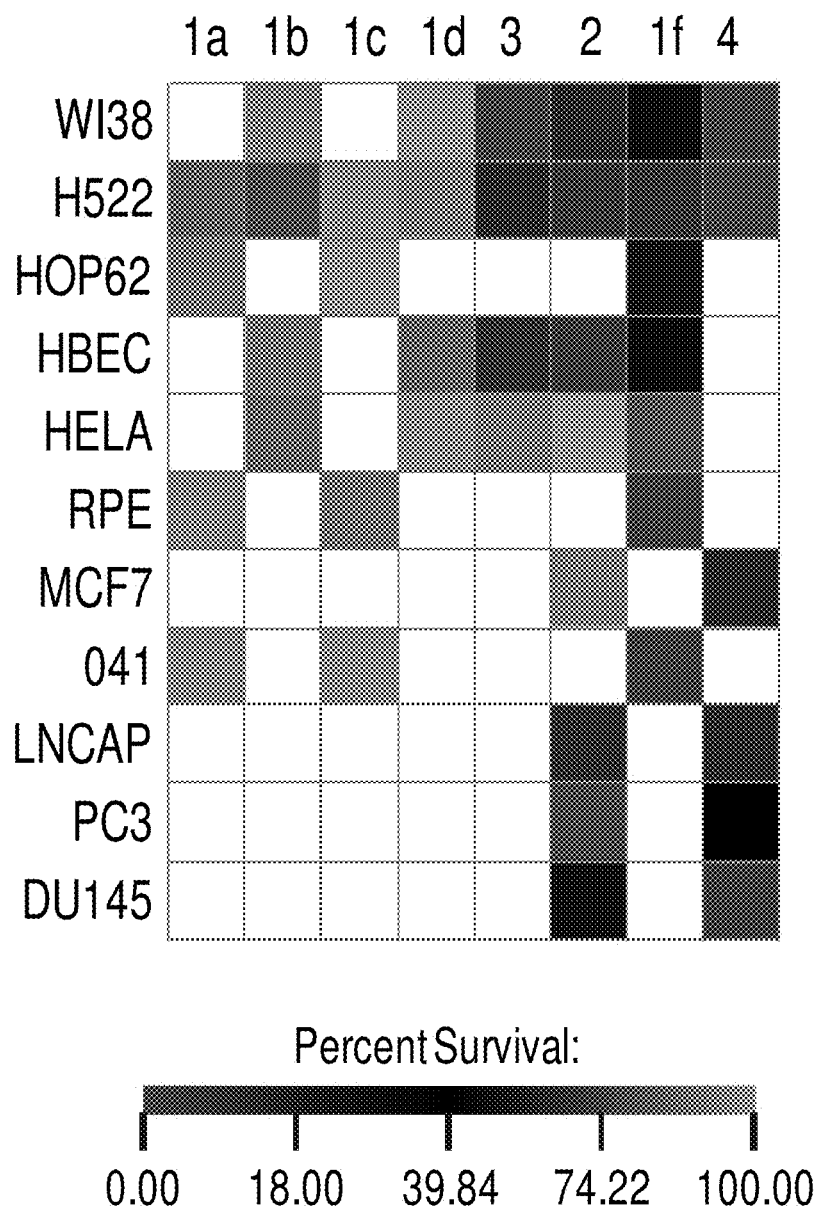
FIG. 2: The effect of compounds 2, 3, and 4 on cell viability of various cell lines.

The ketone 3, which is a precursor of 2, was also lethal to NCI-H522 cells and has a similar selectivity profile. Compound 4, which is the α-benzyl derivative of 3, was synthesized by treating the ketone 3 with LDA followed by benzyl bromide, and desilylating the product to obtain 4, as depicted in FIG. 6. The α-benzylation did not compromise compound 4's activity on the NI-H522 cell line, thus providing a SAR neutral site for chemical modification. The effects of compounds 2, 3, and 4 on various cell lines are shown in FIG. 2.

Certain embodiments of the compounds disclosed herein are defined in the examples herein. It should be understood that these examples, while indicating particular embodiments of the invention, are given by way of illustration only. From the above discussion and these examples, one skilled in the art can ascertain the essential characteristics of this invention, and without departing from the spirit and scope thereof, can make various changes and modifications of the invention to adapt it to various usages and conditions.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof. Therefore, it is intended that the invention not be limited to the particular embodiment disclosed herein contemplated for carrying out this invention, but that the invention will include all embodiments falling within the scope of the claims.

What is claimed is:

1. A compound of the following structural formula:

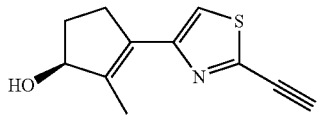

Formula III and salts, stereoisomers, racemates, prodrugs, solvates, and hydrates thereof.

2. A compound consisting of a 4-cyclopentyenyl-2-ethynylthiazole skeleton and a terminal alkyne at the 2-position of a thiazole ring in the 4-cyclopentyenyl-2-ethynylthiazole skeleton.

* * * * *